United States Patent [19]

Imai et al.

[11] Patent Number: 4,717,781

[45] Date of Patent: Jan. 5, 1988

[54] PROCESS FOR THE DEHYDROGENATION OF DEHYDROGENATABLE HYDROCARBONS

[75] Inventors: Tamotsu Imai, Mount Prospect; Jeffery C. Bricker, Buffalo Grove; Tai-Hsiang Chao, Mount Prospect; Maureen L. Bricker, Buffalo Grove, all of Ill.

[73] Assignee: UOP Inc., Des Plaines, Ill.

[21] Appl. No.: 28,844

[22] Filed: Mar. 23, 1987

[51] Int. Cl.$^4$ .............................................. C07C 4/02
[52] U.S. Cl. ..................................... 585/441; 585/906
[58] Field of Search ........................................ 585/441

[56] References Cited

U.S. PATENT DOCUMENTS

| | | | |
|---|---|---|---|
| 3,380,931 | 4/1968 | Ryland | 252/432 |
| 3,437,703 | 4/1969 | Reitmeier et al. | 260/669 |
| 3,670,044 | 6/1972 | Drehman et al. | 260/683.3 |
| 3,855,330 | 12/1974 | Mendelsohn et al. | 260/669 R |
| 3,966,644 | 6/1976 | Gustafson | 252/455 R |
| 3,990,964 | 11/1976 | Gustafson | 208/216 |
| 4,028,227 | 6/1977 | Gustafson | 208/216 |
| 4,391,740 | 7/1983 | Gibson | 252/470 |
| 4,394,303 | 7/1983 | Gibson | 252/470 |
| 4,435,607 | 3/1984 | Imai | 585/443 |
| 4,489,173 | 12/1984 | Gibson | 502/313 |
| 4,495,307 | 1/1985 | Clements | 502/305 |

Primary Examiner—Curtis R. Davis
Attorney, Agent, or Firm—Thomas K. McBride; John F. Spears, Jr.; John G. Tolomei

[57] ABSTRACT

Unsaturated hydrocarbons may be prepared by subjecting a dehydrogenatable hydrocarbon to dehydrogenation in the presence of a dehydrogenation catalyst. The effluent stream from this step, comprising unconverted hydrocarbons, dehydrogenated hydrocarbons, hydrogen and steam, may then be passed to a selective oxidation step in which the hydrogen is selectively oxidized in the presence of an oxygen-containing gas to the substantial exclusion of the oxidation of the hydrocarbons. The oxidation catalyst which is employed will comprise a Group VIII noble metal, a Group IVA metal and a Group IA or IIA metal composited on a metal oxide support. The metal oxide support such as alumina will possess a particular configuration having one or more open channels such as a tubular or cartwheel particle having an outside to inside diameter ratio of the channels ranging from 1.1 to 8 and having a ratio of shape surface to catalyst volume greater than [4D+2L] in which D is the largest representative diameter of the particle and L is the length of the particle.

19 Claims, 2 Drawing Figures

PROCESS FOR THE DEHYDROGENATION OF DEHYDROGENATABLE HYDROCARBONS

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reactions continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and high styrene selectivity are achievable.

The combustion of hydrogen with the oxygen in the oxygen-containing gas requires the presence of an oxidation catalyst. There are some key requirements for the oxidation catalyst to be useable for such a purpose. The most important catalytic property required is good catalytic stability since the oxidation catalyst must survive under very severe reaction conditions, namely at about 600° to 650° C. in the presence of steam. Under such conditions, porous inorganic materials such as aluminas, silicas and zeolites cannot maintain their pore structures for a long period of time, resulting in the permanent damage of catalysts prepared using such materials as supports, e.g., platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide, graphite with a major portion of a phosphate species. In addition to these dehydrogenation catalysts, the reaction also employs a catalyst for the oxidation step of the process comprising platinum or palladium in elemental form or as a soluble salt. Another U.S. patent, namely U.S. Pat. No. 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular sieves zeolite-type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a low selectivity to carbon monoxide and carbon dioxide. In addition, the patentee teaches the use of one catalyst for both dehydrogenation and oxidation which is in contrast to the separate dehydrogenation and oxidation catalysts which are used in the present process.

In addition to the aforementioned U.S. patents, another patent, namely U.S. Pat. No. 4,435,607 also discloses a method for the dehydrogenation of dehydrogenatable hydrocarbons utilizing a two-step process which includes dehydrogenation followed by a selective oxidation process. The catalyst which is employed for the selective oxidation will comprise a noble metal of Group VIII, a metal of Group IVA and, if so desired, a metal of Group IA or IIA of the Periodic Table composited on a highly porous inorganic support. The catalyst base which is used to prepare the oxidation catalyst in this patent was prepared from particles which were relatively small in size.

Prior U.S. patents have disclosed shaped catalyst particles for use in various processes involving petroleum. For example, U.S. Pat. No. 4,495,307 discloses a shaped catalyst which is used in the hydroprocessing of petroleum oils. The catalyst, which comprises a hydrogenation metal selected from Group VIB and Group VIII on a porous inorganic oxide substrate, is utilized to treat a petroleum oil feedstock, the particular shape of the catalyst being utilized to provide a catalyst which possesses a relative strength which is capable of withstanding pressures or stresses which are normally encountered during the processing of the oil. U.S. Pat. No. 4,391,740 also discloses a shaped hydroprocessing catalyst utilized for treating heavy carbonaceous feedstocks. The purpose of these shaped catalysts is to increase a surface to volume ratio whereby increased metal loadings may be afforded. Again the catalyst may contain metals from Groups VIB and VIII of the Periodic Table, specific examples of these metals being molybdenum, tungsten, nickel, and cobalt. Likewise, U.S. Pat. No. 4,394,303 also discloses a shaped catalyst similar in nature to the catalyst of the previously mentioned patent. This catalyst is used for treating or hydroprocessing heavy hydrocarbonaceous feedstocks which contain nickel and vanadium.

Another patent, namely U.S. Pat. No. 4,489,173, discloses a shaped catalyst similar in nature to that described in U.S. Pat. No. 4,391,740, said catalyst also containing a catalytic metal from Group VIB and, if so desired, a catalytic metal of Group VIII in which the shape of the catalyst comprises a cross section which is oval in configuration and having at least one section extending from the flat surface of the oval. U.S. Pat. No. 3,966,644 describes a shaped catalyst particle utilized for hydrotreating petroleum oils. The catalyst base comprises a silica-alumina compound having molybdenum, cobalt or nickel or mixtures thereof impregnated thereon. The catalyst shape may vary from oval to dumbbell to polylobular in configuration. U.S. Pat. No. 3,990,964 discloses a process for hydrotreating a petroleum distillate to remove sulfur-containing and nitrogen-containing components utilizing, as the hydrotreating catalyst, a composition similar in nature to the catalyst described in the preceding patent. In addition to these patents, U.S. Pat. No. 4,028,227 discloses a process for hydrotreating a petroleum residuum with a catalyst of this type to obtain a desulfurized product.

As will hereinafter be shown in greater detail, we have now discovered that by utilizing a selective oxidation catalyst in which the substrate has an open channel configuration, it is possible to effect a selective oxidation process and to obtain a greater yield of desired products with a correspondingly increased stability and conversion over the processes which have utilized catalysts in which the substrate is spherical or cylindrical in nature.

BRIEF SUMMARY OF THE INVENTION

This invention relates to a process for the dehydrogenation of dehydrogenatable hydrocarbons. More specifically, the invention is concerned with a process for the dehydrogenation of a dehydrogenatable hydrocarbon in which the hydrocarbon which is to undergo treatment is subjected to a dehydrogenation step in the presence of a dehydrogenation catalyst. This dehydrogenation step is followed by a selective oxidation step in which the product mixture which results from the aforementioned dehydrogenation step is treated in the presence of certain catalytic compositions of matter which are hereinafter set forth in greater detail in such a manner whereby the hydrogen which is present and which has resulted from the dehydrogenation step is selectively oxidized with a concomitant minimum oxidation of the hydrocarbons. By utilizing the particular support for the selective oxidation catalyst, it is possible to obtain the desired dehydrogenated hydrocarbons in a relatively high yield as well as maintaining the stability and activity of the catalyst to a greater degree than has heretofore been experienced. By maintaining the aforementioned stability and activity, it is possible to obviate the necessity for relatively frequent changes of the catalyst or, in the alternative, regenerating the catalyst, thereby adding to the commercial attractiveness and economical feasibility of the dehydrogenation process.

By utilizing a catalyst in which the base or substrate upon which the catalytic metals are impregnated has an open channel configuration, it is possible to obtain an increase in the effectiveness of the catalyst. The effectiveness factor of the catalyst will be measured by the effective active sites divided by the total active sites. This may also be translated to equate the effectiveness factor as equalling the effective catalytic metal content divided by the total catalytic metal content which is impregnated on the surface of the substrate. By utilizing the particular configuration, it is possible to increase the number of effective active sites containing the catalytic metal, thereby increasing to a great extent the effectiveness factor of the finished catalyst composite.

It is therefore an object of this invention to provide a process for the dehydrogenation of dehydrogenatable hydrocarbons.

A further object of this invention is to provide a catalyst for the selective oxidation step of the dehydrogenation process whereby the hydrogen which is formed during the dehydrogenation step will be selectively oxidized by the oxidation catalyst to the substantial exclusion of the oxidation of the hydrocarbons in the feedstock at a more effective rate than was heretofore found.

In one aspect, an embodiment of this invention resides in a process for the dehydrogenation of a dehydrogenatable hydrocarbons with separate and intermediate selective oxidation of hydrogen which comprises the steps of:

(a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam;

(b) removing said first-reaction dehydrogenation zone effluent from said first-reaction dehydrogenation zone;

(c) passing said effluent of step (b) to a second-reaction oxidation zone, which is separate and discrete from said first-reaction dehydrogenation zone;

(d) contacting said first-reaction dehydrogenation zone effluent in said second-reaction oxidation zone with an oxygen-containing gas to selectively oxidize said hydrogen within said first-reaction zone effluent to the substantial exclusion of oxidation of unconverted and dehydrogenated hydrocarbons in the presence of an oxidation catalyst consisting essentially of a Group VIII noble metal, a Group IVA metal and a Group IA or IIA metal composited on a metal oxide support at oxidation conditions wherein the exothermic selective oxidation of said hydrogen provides additional heat and thereby raises the temperature of said unconverted and dehydrogenated hydrocarbons;

(e) withdrawing said unconverted and dehydrogenated hydrocarbons from said second-reaction oxidation zone having an increased temperature with respect to the temperature of said first-reaction dehydrogenation zone effluent;

(f) passing said removed second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and, (g) withdrawing and recovering said dehydrogenated hydrocarbons, the improvement which comprises utilizing as said support a shaped particle having one or more open channels wherein the channels have an outside diameter, $d_o$, to inside diameter, $d_i$, ratio greater than 1.10 and less than 8.0, where $d_i$ is the largest transverse dimension across the inside of any channel and $d_o$ is the dimension to the outside of the walls surrounding the channel, taken along the line of dimension $d_i$, and the entire particle having a ratio of shape surface to gross volume greater than $[4/D + 2/L]$ in which D is the average overall diameter of the particle in a direction transverse to the axis of the channels and L is the average channel length.

A specific embodiment of this invention is found in the process for the dehydrogenation of ethylbenzene which comprises contacting said ethylbenzene with a dehydrogenation catalyst comprising an alkaline metal-modified iron catalyst at a temperature in the range of from about 500° to about 700° C. and a pressure in the range of from about 0.1 (0.1013 kPa) to about 10 (10.133 kPa) atmospheres in the presence of steam, thereafter contacting the resultant mixture of unconverted ethylbenzene, styrene, hydrogen and steam with air at a temperature in the range of from about 500° to about 700° C. and a pressure in the range of from about 0.1 (0.1013 kPa) to about 10 (10.133 kPa) atmospheres in the presence of a catalyst comprising a mixture of platinum, tin and lithium composited on a tubular alpha-alumina supported particle in which the outside to inside diameters are in a ratio of from 1.10 to about 8.0 and the length, L of the channels to the inside diameter $d_i$ is in a ratio of from 0.25 to about 1.00 whereby hydrogen is selectively oxidized to the substantial exclusion of the oxidation of the ethylbenzene and styrene and recovering the desired styrene after the final stage of dehydrogenation.

Other objects and embodiments will be found in the further detailed description of the invention.

DETAILED DESCRIPTION OF THE INVENTION

As hereinbefore set forth, the present invention is concerned with a dehydrogenation process for the dehydrogenation of dehydrogenatable hydrocarbons which involves the use, in one step of the process, of a selective oxidation catalyst which will provide both improved stability of the catalyst as well as an increase in the conversion rate of the dehydrogenatable hydrocarbons and the selectivity to the desired products.

The catalyst which is employed for this selective oxidation step must possess certain characteristics which are relatively critical in nature in order to obtain the desired results. For example, the catalytic stability and effectiveness of the active elements of the selective oxidation catalyst are often low, due to pore diffusional resistance. In addition, it is also important that there be a relatively low pressure drop across the oxidation catalyst bed inasmuch as dehydrogenation reactions are often adversely affected by a pressure increase. The importance of the particle size in a catalyst is due to the pressure drop which is associated with catalyst particles which are relatively small in size. In addition, the effectiveness factor of the catalyst is related to the ratio of effective active sites to the total active sites. In order to provide a catalyst which possesses a maximum number of effective active sites, it is necessary to provide a support which possesses a particular shape, whereby the greatest effective amount of catalytic metal may be deposited on the surface of the support, while at the same time providing a minimum amount of active metal loadings.

With respect to the particle size, for example, when utilizing processes such as a stacked bed setup, in which the dehydrogenation catalyst and the oxidation catalyst are present in two distinct or discrete layers or beds, an undesirable pressure drop may be created by the presence of the oxidation catalyst. In many dehydrogenation reactions the conversion of the dehydrogenatable hydrocarbon is relatively sensitive to the pressures which are employed to effect the conversion. For example, in the conversion of ethylbenzene to styrene, as the pressure which is employed increases, the equilibrium conversion level decreases in a significant manner.

In view of the effect of pressure hereinbefore discussed, one of the critical parameters of an effective selective oxidation catalyst is flow resistance of a bed of particles or supports upon which the metallic components of the system are composited. The flow resistance of the catalytic particle bed must be low enough so that the pressure drop in the process which is usually associated with the catalyst, does not limit the conversion of the dehydrogenatable hydrocarbon to the dehydrogenated hydrocarbon. The open channel configuration has been found to greatly reduce the pressure drop of a catalyst bed composed of such particles. In addition, the active sites, i.e., those which contain the catalytic metal or combination of catalytic metals, must be readily available to contact with the hydrocarbon feed. In view of the fact that the support or substrate upon which the catalytic metal or metals are composited, is porous in nature, it is imperative that the active catalytic metals must not be too deeply impregnated into the pores but must be in a position on or adjacent to the exterior surface of the support in order that they may afford ready contact with the aforesaid feed. By utilizing a catalyst support base of the type hereinafter set forth in greater detail, it has now been found that the effective active sites as defined by the effective catalytic metal may be found over a much wider surface of the base, and will afford more ready contact with the feed, thereby increasing the effectiveness of the catalyst. This increase in effectiveness will be illustrated by the increased catalytic activity of the selective oxidation catalyst along with a concurrent greater stability thereof. By utilizing a particular catalyst shape of the present invention, it is possible to obtain a catalyst system for use in a selective oxidation process whereby extremely high conversion of the starting materials and a concurrent high selective oxidation of hydrogen, which is a by-product of the dehydrogenation process to the substantial exclusion of oxidation of the unconverted and dehydrogenated hydrocarbons, may be obtained.

BRIEF DESCRIPTION OF THE DRAWING

As an illustration of two types of channel configurations that may be used for the support particles.

Figure 1:
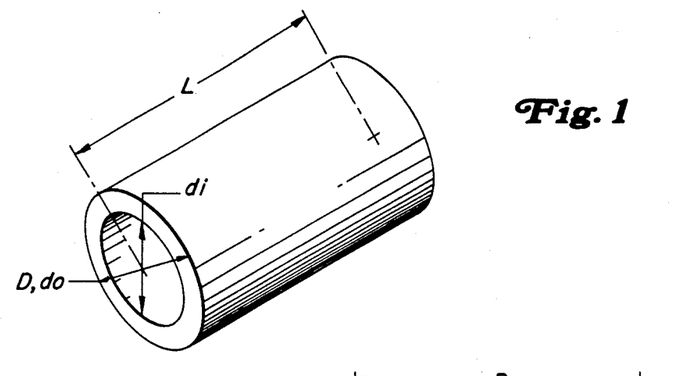
FIG. 1 represents a perspective side-view of a catalyst support particle which is tubular in configuration and FIG. 2 illustrates a cross-sectional view of a tubular catalyst having interior section of the tube filled with a plurality of intersecting vanes that give the particle a cartwheel shape.
Figure 2:
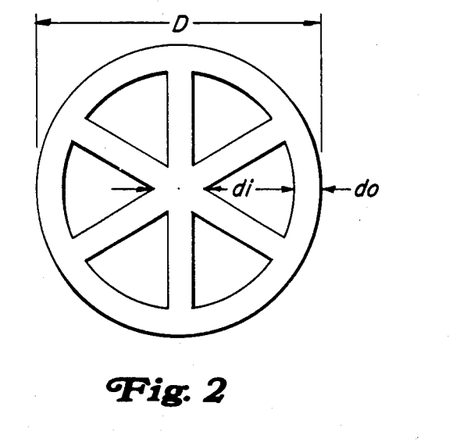

It is to be understood that the tubular or cartwheel shaped catalyst particles are given only for purposes of illustration and that a wide variety of geometric shapes, including honeycomb structures can provide the open channel configuration of the particle. In the Figures, "L" will represent the length of the entire particle and "D" will represent the average outside diameter of the entire particle. The inside diameter of any given channel is designated as "$d_i$"; and the outside diameter of the channel along the length of any given inside diameter is designated "$d_o$."

FIG. 1 demonstrates that for the simplest channel configuration, that of a cylindrical tube, D equals $d_o$ and $d_i$ is simply the inner tube dimension. This will not be the case for more complicated channel structures as shown by the depiction of D, $d_o$, and $d_i$ on FIG. 2.

In the present process, a dehydrogenatable hydrocarbon of the type hereinafter set forth in greater detail is contacted with a dehydrogenation catalyst in the presence of steam in a multicatalyst bed system. Inasmuch as the dehydrogenation of the hydrocarbon is endothermic in nature, it is necessary to provide an additional amount of heat before the product enters the next catalyst bed in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen, with the resultant composition thereof, is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidation catalyst, both of the type hereinafter set forth in greater detail, are loaded in the apparatus in alternate layers. The number of alternate layers of dehydrogenation catalyst and selective oxidation catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which include lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassium hydroxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition to these catalysts, other well-known dehydrogenation catalysts which may be utilized will include those comprising ferric oxide, potassium oxide, as well as other metal oxides and/or sulfides of metals of Groups IA, IIA, IVB, VB and VIB of the Periodic Table including those of calcium, lithium, strontium, magnesium, beryllium, zirconium, tungsten, molybdenum, hafnium, vanadium, copper, chromium and mixtures of two or more oxides such as chromia-alumina, chromia-titania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C. and at a reaction pressure in the range of from about 0.1

(0.1013 kPa) to about 10 (10.133 kPa) atmospheres; the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention. After contacting the dehydrogenation catalyst with the steam and hydrocarbon, the resulting mixture comprising unconverted hydrocarbon, dehydrogenated hydrocarbon, steam and hydrogen which has passed through the catalyst bed is contacted in a separate zone with the selective oxidation catalyst composition of the type hereinafter set forth in greater detail. In addition, oxygen-containing gas is introduced into the reactor, preferably at a point adjacent to the oxidation catalyst bed. Examples of oxygen-containing gases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidation catalyst whereby hydrogen is selectively oxidized to water with a minimal amount of reaction of oxygen with the hydrocarbons, either unconverted hydrocarbon or dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenatable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isqpropyltoluene, ethylnaphthalene, propylnaphthalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as ethylene, propylene, 1-butene, 2-butene, 1-pentene, 2-pentene, 1-hexene, 2-hexene, 3-hexene, and branched chain derivatives thereof, etc.

The selective oxidation step of the process utilizes, as hereinbefore set forth, the hydrogen which has been produced in the dehydrogenation step of the process to supply heat to the inlet of the next dehydrogenation catalyst bed. Inasmuch as temperatures which are utilized in the process may be as high as 650° C. in the presence of steam, the operating conditions in which the oxidation catalyst must function are severe in nature. In order for the oxidation catalyst to remain stable and minimize the carbon formation thereon, the catalyst support must be calcined at a relatively high temperature in order to decrease the micropore surface area, this decrease in micropore surface area contributing to the stability of the catalyst. Conventional oxidation catalysts utilizing a porous support such as alumina which had been calcined at relatively low temperatures, i.e., below about 900° C. or lower, lose surface area at a rapid rate and form excessive carbon on the surface thereof, thus resulting in a deactivation of the catalyst.

An effective oxidation catalyst which may be used in the dehydrogenation and selective oxidation process of the present invention comprises a noble metal of Group VIII of the Periodic Table such as platinum along with a Group IVA metal of the Periodic Table such as tin and, if so desired, a metal selected from Group IA and IIA of the Periodic Table composited on a solid porous inorganic oxide support. A particularly effective support which contributes to the stability and effectiveness of the catalyst comprises an alumina. We have now discovered that certain aluminas may be selected as the precursor for the support which will, after peptizing of the precursor and calcination, provide a support for the catalytic metals of the composite, the final composite possessing the necessary stability to effectively operate as an efficient catalyst over a relatively long period of time. The alumina support will be derived from various types of aluminas such as, for example, boehmite, pseudoboehmite, gibbsite, etc. which possess certain desirable properties or characteristics. The alumina must be a low density compound in which the Apparent Bulk Density (ABD) is preferably less than about 1.3 g/cc, the pore volume greater than about 0.2 cc/g, the pore distribution such that more than 1% of the total pore volume is present in pores greater than 300 angstroms in diameter, and a surface area of from about 1.0 to about 400 m$^2$/g. By utilizing such a precursor, it is possible after peptizing of the precursor and calcination, to obtain a finished catalyst support which will provide the enhanced stability which is desired to be present in the final catalyst composite. The calcination of the alumina support is effected at a temperature within the range of from about 600° to about 1500° C. prior to impregnation of the metals thereon. If so desired, the calcination of this support may be effected in a dry atmosphere, preferably at a temperature in the range of from about 1100° to about 500° C. or the calcination may be effected in a hydrous atmosphere such as that provided by steam, the temperatures preferably in the range of from about 900° to about 1400° C. The calcination of the support within these temperature ranges will be effected over a period of time which may range from about 0.5 to about 30 hours or more in duration and it is to be understood that the particular temperature which is selected for the calcination of the support will influence or direct the time frame during which the calcination takes place.

The alumina support which is recovered from the calcination step will, in the preferred embodiment of the invention, also possess certain desirable characteristics or properties. For example, the ABD of the finished support will preferably be in a range of from about 0.1 to about 1.3 g/cc, the pore volume greater than about 0.2 cc/g, the surface area in a range of from about 1 to about 400 m²/g, the piece density in a range of from about 0.3 to about 2.5 g/cc, and a pore distribution such that more than 1% of the pore volume is present in pores greater than 1000 angstroms in diameter.

As will hereinafter be shown in greater detail, the use of a support possessing the properties and sizes will result in the obtention of a catalyst composite which will exhibit greater stability and selectivity as well as a lower pressure drop when employed in the selective oxidation process than will be found when utilizing catalyst supports which possess properties and particle sizes outside the range set forth for the low density alumina precursors.

As was hereinbefore set forth, the selective oxidation catalysts which are employed in the process of this invention will comprise a noble metal of Group VIII of the Periodic Table and a metal of Group IVA of the Periodic Table composited on a solid inorganic support which, prior to the compositing of the metals thereon, has been peptized and thereafter calcined at a temperature within the range hereinbefore discussed. In addition, if so desired, it is also contemplated within the scope of this invention that the catalyst will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight, preferably in an amount in the range of from about 0.01% to about 2% by weight. Of the metals of Group IVA of the Periodic Table, germanium, tin and lead comprise the preferred species, these metals also being present in the final catalyst composite in an amount in the range of from about 0.01% to about 5% by weight, preferably in a range of from about 0.05% to about 2% by weight. The preferred species of metals of Group IA or IIA of the Periodic Table will include lithium, sodium, potassium, rubidium, cesium, beryllium, magnesium, calcium, barium, francium, and radium, the alkali metals or alkaline earth metals being present in an amount in the range of from about 0.01% to about 10% by weight, preferably in an amount in the range of from about 0.05% to about 5% by weight of the catalyst composite.

The selective oxidation catalyst which utilizes, as the support for the metallic portion of the composite an alumina, may be prepared in any suitable manner known in the art. For example, the alumina may, in one form of preparation, be impregnated with an aqueous solution of a metal of Group IVA of the Periodic Table, the amount of soluble salts such as tin chloride, tin bromide, tin sulfate, lead chloride, lead persulfate, germanium chloride, etc. being present in the solution sufficient so that the catalytic composition will contain the desired amount of metals. The impregnated support will then be peptized with an acid such as nitric acid. The type of acid used for peptization may be varied, for example, acetic acid, carbonic acid, or hydrochloric acid may be employed. The resulting impregnated support, in the form of a dough, is then extruded through a dye, the orifice of the dye determining the cross-sectional shape of the support including the number of open channels which the finished catalyst composite will possess. After extrusion, the dough is then calcined at a temperature of about 600° C. for a period of time ranging from about 1 to about 12 hours in an air or air/steam atmosphere, followed by a high temperature calcination in a range of from about 1,000 to about 1500° C. for a period of from about 1 to about 8 hours.

The thus calcined base may then be coimpregnated with an aqueous solution containing soluble salts of Group VIII noble metals and Group IVA of the Periodic Table and, if so desired, a metal of Group IA or IIA. Examples of soluble salts of the noble metals of Group VIII of the Periodic Table which may be used include chloroplatinic acid, chloropalladic acid, rhodium chloride, platinum sulfate, palladium sulfate, etc. Examples of Group IV soluble salts will include tin chloride, tin bromide, tin iodide and tin sulfate. Examples of soluble salts of Group IA or IIA metals will include potassium chloride, potassium bromide, potassium iodide, potassium nitrate, potassium sulfate, potassium acetate, potassium propionate, rubidium chloride, rubidium bromide, rubidium iodide, rubidium nitrate, rubidium sulfate, rubidium acetate, rubidium propionate, cesium chloride, cesium bromide, cesium iodide, cesium nitrate, cesium sulfate, cesium acetate, cesium propionate, calcium chloride, barium chloride, barium bromide, barium iodide, barium nitrate, barium sulfate, barium acetate, barium propionate, etc.

After allowing the coimpregnation of the base to proceed for a period of time sufficient to permit the deposition of the desired amounts of metals within the range hereinbefore set forth, the composite is recovered, dried and calcined at a temperature in the range of from about 500° to about 650° C. or more in a steam atmosphere.

The impregnation of Group VIII, Group IVA, and Group IA or IIA metals may also be performed in a step-wise manner, if desired, rather than coimpregnation.

The incorporation of Group IVA metal may also be carried out in the support forming step. Tin, for example, may be added in the preparation of the alumina support whether it be by oil-dropping of spheres or extrusion of alumina dough. The tin incorporation may also be a combination of tin in sol and impregnated tin.

As was hereinbefore set forth, the channeled catalyst particles will contain more active sites of catalytic metals than will catalysts of conventional shapes such as beads, spheres, pellets, etc. and at the same time, effect this increased active sites with a lower amount of metal loading. The catalytic particles may range in length from about 0.050 to about 0.75 inches and will have a ratio of shape surface to gross catalyst volume greater than $[4/D + 2/L]$, where D is the average outside diameter of the entire particle and L is the length of the extrudate. The term shape surface refers to the macroscopic surface area of the support for all surfaces of the support, including the interior walls of the channels and excludes the surface area associated with any microscopic pores. The term gross volume means the solid support volume which includes the volume of the channels. The relative inside and outside diameters of the channels are limited to provide to a ratio of $d_o/d_i$ which is between 1.1 and 8.0 where $d_i$ is the largest transverse dimension across the inside of any channel and $d_o$ is the dimension to the outside of walls surrounding the channel, taken along the line of dimension $d_i$. This ratio of channel diameters is chosen to provide channels large enough for flow purposes and adequate wall thickness around the channels for structural integrity of the support. By forming a catalyst which possesses these particular configurations, it is possible to obtain a catalyst which possesses a greater effectiveness factor with a corresponding stability than was obtained when utilizing catalysts of more conventional shapes.

Some specific examples of selective oxidation catalytic compositions of matter which may be used in the process of the present invention comprise, as hereinbefore set forth, the noble metals of Group VIII, a metal of Group IA or IIA, a metal of Group IVA, composited on a theta or alpha-alumina which has been calcined at a temperature within the ranges hereinbefore set forth. These examples will include platinum, germanium and lithium composited on alumina, palladium, germanium and potassium composited on alumina, rhodium, germanium and potassium composited on alumina, platinum, tin and potassium composited on alumina, palladium, tin and potassium composited on alumina, rhodium, tin and potassium composited on alumina, platinum, germanium and cesium composited on alumina, palladium, germanium and cesium composited on alumina, rhodium, germanium and cesium composited on alumina, platinum, tin and cesium composited on alumina, palladium, tin and cesium composited on alumina, rhodium, tin and cesium composited on alumina, platinum, germanium and barium composited on alumina, palladium, germanium and barium composited on alumina, rhodium, germanium and barium composited on alumina, platinum, tin and barium composited on alumina, palladium, tin and barium composited on alumina, rhodium, tin and barium composited on alumina, platinum, lead and potassium composited on alumina, palladium, lead and potassium composited on alumina, rhodium, lead and potassium composited on alumina, etc. It is to be understood that the above-enumerated catalysts are only representative of the selective oxidation catalyst composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated.

By utilizing the particular shaped support upon which the catalytic metals are impregnated, it is possible to obtain a catalyst which exhibits the desired characteristics of stability and activity which is in contradistinction to prior art types of oxidative catalysts which cannot produce the desired stability exhibited by the present catalysts, and therefore cannot survive in use for a long period of time. This relatively short life of a catalyst discourages the commercial use of such catalysts as unattractive due to the necessity of having to replace or regenerate the catalyst after a short interval of operating time has elapsed. In addition, the catalysts of the present invention also exhibit a definite activity for the selective oxidation of hydrogen rather than a tendency for the oxidation of the dehydrogenated products or unreacted hydocarbons.

The particular effectiveness of the catalyst of the present invention which possesses a channeled configuration will be hereinafter shown in greater detail in the examples. The catalyst of the present invention will exhibit an excellent stability in that it possesses the ability to maintain the maximum temperature of the reaction at a position which is near the inlet of the catalyst bed. The desired reaction, that is, the selective oxidation of hydrogen, is highly exothermic in nature and it is therefore an indication of a good catalyst that the maximum temperature is maintained near the inlet of the catalyst bed, thus indicating that the conversion of the hydrogen occurs at a time shortly after the product stream comprising unconverted hydrocarbons, dehydrogenated hydrocarbons, steam and hydrogen enters the catalyst bed. In addition, as will hereinafter be demonstrated, the catalyst of the present invention also possesses the ability to effect a relatively high conversion of oxygen as is evidenced by the absence of oxygen in the exit gas which is withdrawn from the reaction zone containing the selective oxidation catalyst.

The following examples are given for purposes of illustrating the selective oxidation catalyst of the present invention as well as to a process utilizing the selective oxidation catalyst in said process. However, it is to be understood that these examples are merely illustrative in nature and that the present process is not necessarily limited thereto.

EXAMPLE I

Selective oxidation catalysts were prepared by adding a solution comprising 37.0 g of nitric acid per kg of alumina and in 1.18 kg of water per kg of alumina to boehmite powder which had an ABD of less than 0.8 g/cc and a pore volume of greater than 0.2 g/cc. The powder and solution were stirred for a period of about 6 minutes and the resultant dough was extruded through an extruder having a stainless steel dieplate. In one extrusion, the orifice of the dieplate was circular in configuration while in the other extrusion the orifice of the dieplate was annular in configuration. The extrudate products were dried for a period of 3 hours at 100° C. in a forced draft oven. The resulting material was then precalcined after recovery from the drying procedure by raising the temperature from ambient to 350° C. in a 1 hour period in a flowing air atmosphere. The temperature was maintained at 350° C. for a period of 1 hour, following which the temperature was increased to 600° C. during a period of 1 hour. The temperature was maintained at 600° C. in a flowing air atmosphere for an additional period of 3 hours, following which the extrudate was allowed to cool to ambient temperature over a period ranging from 4 to 8 hours. High temperature calcination of the extrudate was accomplished by heating the extrudate from ambient temperature to 1330° C. during a period of 10 hours in a muffle furnace. After reaching 1330° C., the temperature was maintained thereat for a period of 3 hours, following which the extrudate was slowly cooled during a period of 10 hours to less than 300° C.

The catalyst composite was then prepared by charging a solution containing platinum, tin, and lithium salts in deionized water to an Erlenmeyer flask in an amount so as to afford 0.4 wt. % platinum, 0.5% Sn, and 0.2% Li based on the weight of the calcined support. Thereafter, nitric acid was added to the same flask and sufficient deionized water was also charged to the flask to afford an impregnating solution/calcined support ratio of 1/1

(volume/volume). The impregnating solution was added to a glass-jacketed rotary evaporator and thereafter the calcined support was also added to the evaporator. A nitrogen purge was initiated while the mixture was cold rolled for a period of 15 minutes. Following the cold roll, steam was charged to the evaporator jacket and the liquid was allowed to evaporate until the presence of moisture was not detectable at the mouth of the evaporator.

The catalyst composite was dried in a forced draft oven at a temperature of 150° C. for a period of 2 hours and subsequently loaded into a quartz tube which was placed in a furnace. The catalyst composite was then calcined by raising the heat in the furnace from ambient to 650° C. during a period of 2 hours while passing a stream of air over the composite. When the temperature of the catalyst bed reached 650° C., a stream of air was passed over the composite which had been passed through water heated to a temperature of 650° C. The temperature was maintained at 650° C. while the air/steam atmosphere was passed over the surface of the catalyst for a period of 2 hours. At the end of the 2 hour period, the addition of steam was discontinued while maintaining the temperature at this rate in an atmosphere of air for an additional period of 1 hour. At this time heating was discontinued and the catalyst composite was allowed to return to ambient temperature while maintaining a flowing air atmosphere.

The resulting catalyst composites possessed the following properties:

TABLE I

| SHAPE | METAL LOADINGS | | |
|---|---|---|---|
| | Pt | Sn | Li |
| Cylindrical | 0.4 | 0.5 | 0.2 |
| Tubular | 0.4 | 0.5 | 0.2 |

| | Geometry: | | |
|---|---|---|---|
| SHAPE | OUTSIDE DIAMETER (D) | PARTICLE LENGTH ( ) | INSIDE DIAMETER ($d_i$) |
| Cylindrical | 3.5 mm | 6 mm | — |
| Tubular | 4.5 mm | 6 mm | 2.0 mm |

EXAMPLE II

The catalysts which were prepared according to the above examples were evaluated for conversion of ethylbenzene to styrene with regard to catalyst activity and selectivity for oxygen reacting with hydrogen to form water. The catalysts were loaded into a $\frac{7}{8}''$ inner diameter stainless steel reactor having a 10" long $\frac{1}{2}$ diameter base for the catalyst loading. The reactor inlet temperature was adjusted to maintain a 600° C. maximum temperature and a feedstock comprising a mixture of ethylbenzene, styrene, steam, hydrogen, oxygen and nitrogen which simulated a product stream at about a 60% ethylbenzene conversion from a second dehydrogenation catalyst bed of a 3 dehydrogenation catalyst bed reactor system having an oxidation catalyst bed position between the dehydrogenation catalyst beds was fed to the reactor. The feedstream was passed over the oxidation catalyst bed at the aforesaid inlet temperature and at a reactor outlet pressure of 0.7 atmospheres (0.709 kPa). The hydrocarbon feed was maintained at a Weight Hourly Space Velocity of 34 hours$^{-1}$. The molar feed ratio of ethylbenzene and styrene/$H_2O$/$H_2$/$O_2$/$N_2$ equaled 1.0/9/0.45/0.91/1.

The amount of catalyst which was used in the two tests was 12.0 g of the cylindrical catalyst and 12.0 g of the tubular catalyst; the total amount of platinum loaded in the reactor was 0.048 g for the cylindrical catalyst and 0.048 g for the tubular catalyst.

As an indication of the activity and stability of the catalyst, measurements were taken to determine the position of the maximum temperature which was present in the bed of catalyst. As was previously set forth, the maximum catalyst temperature should be at a location near the inlet position of the catalyst. The desired reaction, which is the selective oxidation of hydrogen, is highly exothermic in nature and one feature which determines the activity, stability and effectiveness of a catalyst composite is the position of the maximum catalyst temperature in the catalyst bed as a function of time on stream. In addition, another indication of catalyst activity and stability is found in the amount of oxygen which is converted in the reaction zone over time.

The results of the selective oxidation tests when employing the two disparate shaped alumina supports are set forth in the tables below. In these tables, the catalyst designated A is the cylindrical-shaped alumina support and Catalyst B is the tubular-shaped catalyst support.

TABLE II

| MAXIMUM CATALYST TEMPERATURE °C. | | |
|---|---|---|
| Hours on Stream | A | B |
| 3 | 599 | 603 |
| 6 | 601 | 611 |
| 9 | 603 | 603 |
| 12 | 601 | 603 |
| 15 | 600 | 601 |
| 18 | 600 | 602 |
| 21 | 600 | 602 |
| 24 | 601 | 601 |

It is noted from the above Table that the maximum catalyst temperature was maintained at a steady rate. As will be shown in the following Table, it was found that the oxygen conversion was substantially lower when utilizing the cylindrical-shaped catalyst than when utilizing the tubular-shaped catalyst.

TABLE III

| OXYGEN CONVERSION | | |
|---|---|---|
| Hours on Stream | A | B |
| 3 | 92.9 | 97.8 |
| 6 | 92.5 | 95.8 |
| 9 | 91.8 | 96.5 |
| 12 | 91.9 | 96 |
| 15 | 91.9 | 94.5 |
| 18 | 91.8 | 95.0 |
| 21 | 91.2 | 94.7 |
| 24 | 91.5 | 94.9 |

The position of the maximum temperature in the catalyst bed is also a criteria as to the effectiveness of the catalyst, inasmuch as a movement or lowering of the maximum temperature in the catalyst bed will indicate a lack of stability of the catalyst which, over a long period of time, would affect the effectiveness of the catalyst to selectively oxidize hydrogen to the exclusion of oxidation of the hydrocarbons. This difference is shown in Table IV below.

TABLE IV

| LOCATION OF MAXIMUM TEMPERATURE IN CATALYST BED (INCHES FROM TOP OF CATALYST BED) | | |
|---|---|---|
| Hours on Stream | A | B |
| 3 | 1.25 | 1.00 |
| 6 | 1.25 | .75 |

TABLE IV-continued

LOCATION OF MAXIMUM TEMPERATURE
IN CATALYST BED
(INCHES FROM TOP OF CATALYST BED)

| Hours on Stream | A | B |
| --- | --- | --- |
| 9 | 1.25 | .87 |
| 12 | 1.25 | .75 |
| 15 | 1.11 | .75 |
| 18 | 1.11 | 1.0 |
| 21 | 1.0 | .87 |
| 24 | 1.25 | .87 |

It is noted from the above Table that the position of the maximum temperature in the catalyst bed when utilizing the tubular-shaped catalyst was much closer to the catalyst inlet position than the position when using the cylindrical-shaped catalyst and in addition, did not indicate downward movement of the maximum catalyst temperature. The significance of this result is amplified by the fact that, due to the lower density of the tubular catalyst, a smaller weight percentage of the tubular catalyst is contacted per unit of length of the bed as compared to the cylindrical catalyst.

An indication of the styrene selectivity of the two catalyst shapes is the concentration of carbon oxides in the reaction zone effluent.

TABLE V $CO_X$ IN TOTAL EFFLUENT, MOL %

| Hours on Stream | A | B |
| --- | --- | --- |
| 3 | .04 | .07 |
| 6 | .03 | .04 |
| 9 | .03 | .05 |
| 12 | .03 | .04 |
| 15 | .03 | .04 |
| 18 | .03 | .04 |
| 21 | .03 | .04 |
| 24 | .02 | .04 |

While the reference catalyst does demonstrate a slightly lower concentration of carbon oxides in the effluent of the reference catalyst, the concentrations for both catalysts are extremely low. Moreover, in light of the overall higher activity of the tubular catalyst, some increase in carbon oxide production over the reference catalyst is expected. In recognition of the overall higher activity for the tubular catalyst, the very small $CO_X$ production for these results show that the tubular catalyst maintains a very good selectivity toward hydrogen combustion.

What is claimed is:

1. In a process for the dehydrogenation of a dehydrogenatable hydrocarbons with separate and intermediate selective oxidation of hydrogen which comprises the steps of:
   (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam;
   (b) removing said first-reaction dehydrogenation zone effluent from said first-reaction dehydrogenation zone;
   (c) passing said effluent of step (b) to a second-reaction oxidation zone, which is separate and discrete from said first-reaction dehydrogenation zone;
   (d) contacting said first-reaction dehydrogenation zone effluent in said second-reaction oxidation zone with an oxygen-containing gas to selectively oxidize said hydrogen within said first-reaction zone effluent to the substantial exclusion of oxidation of unconverted and dehydrogenated hydrocarbons in the presence of an oxidation catalyst consisting essentially of a Group VIII noble metal, a Group IVA metal and a Group IA or IIA metal composited on a metal oxide support at oxidation conditions wherein the exothermic selective oxidation of said hydrogen provides additional heat and thereby raises the temperature of said unconverted and dehydrogenated hydrocarbons;
   (e) withdrawing said unconverted and dehydrogenated hydrocarbons from said second-reaction oxidation zone having an increased temperature with respect to the temperature of said first-reaction dehydrogenation zone effluent;
   (f) passing said removed second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and,
   (g) withdrawing and recovering said dehydrogenated hydrocarbons, the improvement which comprises utilizing as said support a shaped particle having one or more channels wherein the channels have an outside diameter, $d_o$, to inside diameter, $d_i$, ratio greater than 1.10 and less than 8.0 where $d_i$ is the largest transverse dimension taken across the inside of any channel and $d_o$ is the dimension to the outside walls of the walls surrounding the channel, taken along the line of $d_i$ and the entire particle having a ratio of shape surface to gross volume greater than $[4/C. +2/L]$ in which D is the average overall diameter of the particle in a direction transverse to the axis of the channels and L is the average channel length.

2. The process as set forth in claim 1 in which the length of said particle is in a range of from about 0.25 D to about 10 D.

3. The process as set forth in claim 1 wherein the particle is tubular in shape.

4. The process as set forth in claim 3 in which the hollow center is bridged by at least one vane to form multiple channels.

5. The process as set forth in claim 1 in which said dehydrogenation and oxidation conditions include a temperature in the range of from about 500° to about 700° C. and a pressure in the range of from about 0.1013 kPa to about 10.133 kPa.

6. The process as set forth in claim 1 in which said Group VIII noble metal is selected from the group consisting of platinum, palladium and rhodium.

7. The process as set forth in claim 5 in which said Group VIII noble metal is present in said oxidation catalyst in an amount in the range of from about 0.01% to about 5% by weight of said catalyst.

8. The process as set forth in claim 1 in which said Group IVA metal is selected from the group consisting of germanium, lead and tin.

9. The process as set forth in claim 7 in which said Group IVA metal is present in said oxidation catalyst in an amount in the range of from about 0.01% to about 5% by weight of said catalyst.

10. The process as set forth in claim 1 in which said Group IA or IIA metal is selected from the group consisting of sodium, lithium, potassium, rubidium, cesium, beryllium, magnesium, calcium, francium, radium, strontium and barium.

11. The process as set forth in claim 9 in which said Group IA or IIA metal is present in said oxidation catalyst in an amount in the range of from about 0.01% to about 10% by weight of said catalyst.

12. The process as set forth in claim 1 in which said oxygen-containing gas is oxygen.

13. The process as set forth in claim 1 in which said oxygen-containing gas is air.

14. The process as set forth in claim 1 in which said metal oxide support of said oxidation catalyst comprises an alumina.

15. The process as set forth in claim 13 in which said alumina is alpha-alumina.

16. The process as set forth in claim 1 in which said alkaline metals in said dehydrogenation catalyst is selected from the group consisting of Group IA and Group IIA of the Periodic Table.

17. The process as set forth in claim 1 in which said dehydrogenation catalyst contains an oxide or sulfide of a metal selected from the group consisting of Groups IVB, VB and VIB of the Periodic Table.

18. The process as set forth in claim 1 in which said dehydrogenatable hydrocarbon is ethylbenzene and said dehydrogenated hydrocarbon is styrene.

19. The process as set forth in claim 1 in which said dehydrogenatable hydrocarbon is p-ethyltoluene and said dehydrogenated hydrocarbon is p-methylstyrene.

* * * * *

UNITED STATES PATENT AND TRADEMARK OFFICE
CERTIFICATE OF CORRECTION

PATENT NO. : 4,717,781
DATED : January 5, 1988
INVENTOR(S) : Imai et al.

It is certified that error appears in the above-identified patent and that said Letters Patent is hereby corrected as shown below:

In Column 18, line 38: Change "D" to --C--.

Signed and Sealed this

Seventeenth Day of May, 1988

Attest:

DONALD J. QUIGG

*Attesting Officer*       *Commissioner of Patents and Trademarks*